US009465021B2

United States Patent
Schulz (10) Patent No.: US 9,465,021 B2
(45) Date of Patent: Oct. 11, 2016

(54) METHOD FOR METROLOGICALLY DIFFERENTIATING MATERIAL REGIONS OF A PAGE-LIKE, WEB-LIKE OR SHEET-LIKE MATERIAL AND DEVICE THEREFOR

(71) Applicant: PEPPERL + FUCHS GmbH, Mannheim (DE)

(72) Inventor: Enrico Schulz, Mannheim (DE)

(73) Assignee: PEPPERL + FUCHS GmbH, Mannheim (DE)

( * ) Notice: Subject to any disclaimer, the term of this patent is extended or adjusted under 35 U.S.C. 154(b) by 244 days.

(21) Appl. No.: 14/186,086

(22) Filed: Feb. 21, 2014

(65) Prior Publication Data
US 2014/0311236 A1 Oct. 23, 2014

(30) Foreign Application Priority Data

Feb. 21, 2013 (EP) .................................... 13000882

(51) Int. Cl.
*G01L 5/04* (2006.01)
*G01N 33/34* (2006.01)
*B65H 7/12* (2006.01)
*G01B 21/08* (2006.01)

(52) U.S. Cl.
CPC ............ *G01N 33/346* (2013.01); *B65H 7/125* (2013.01); *G01B 21/08* (2013.01); *B65H 2511/13* (2013.01); *B65H 2511/416* (2013.01); *B65H 2511/512* (2013.01); *B65H 2511/516* (2013.01); *B65H 2511/524* (2013.01); *B65H 2557/63* (2013.01); *B65H 2701/194* (2013.01)

(58) Field of Classification Search
None
See application file for complete search history.

(56) References Cited

U.S. PATENT DOCUMENTS

| 4,901,577 A * | 2/1990 | Roberts ................... B41F 33/02 73/159 |
| 2007/0034008 A1* | 2/2007 | Voss ....................... G01N 29/11 73/570 |
| 2013/0247683 A1* | 9/2013 | MacDougall .......... G01N 19/04 73/827 |
| 2014/0102617 A1* | 4/2014 | Hutter ...................... B65B 9/20 156/64 |

FOREIGN PATENT DOCUMENTS

| DE | 102004056710 | 7/2004 |
| DE | 102004056742 A1 | 9/2005 |
| EP | 0894756 A2 | 3/1999 |
| EP | 1731455 A1 | 12/2006 |
| EP | 2039633 A2 | 9/2008 |

OTHER PUBLICATIONS

International Application No. EP 13000882, Search Report, Jul. 19, 2013, 2 pages.

* cited by examiner

Primary Examiner — Michael A Lyons
Assistant Examiner — Jermaine Jenkins
(74) *Attorney, Agent, or Firm* — Hoffman Warnick LLC (57) ABSTRACT

A method and device for metrologically differentiating material regions, namely majority regions and minority regions of a page-like, web-like or sheet-like material. At least one sensor receives a measuring signal of variable amplitude, the amplitude being variable depending on the material region located in a spatial detection range of the sensor. The amplitude is increased by a controllable amplifier. The material is moved relatively to the sensor such that majority regions are located in the spatial detection range of the sensor more frequently than minority regions. The method is characterized in that in phases, in which majority regions undergo examination by means of the sensor, by means of the amplifier regulation of the amplitude to a set point is carried out and the sensor generates a signal "majority region", and that in situations, in which the amplitude undergoes a sufficient change, the sensor generates a signal "minority region".

12 Claims, 5 Drawing Sheets

METHOD FOR METROLOGICALLY DIFFERENTIATING MATERIAL REGIONS OF A PAGE-LIKE, WEB-LIKE OR SHEET-LIKE MATERIAL AND DEVICE THEREFOR

TECHNICAL FIELD

The present invention relates to a method for metrologically differentiating regions of material, namely majority and minority regions of page-like, web-like or sheet-like material.

RELATED ART

In a generic method, use is made of at least one sensor adapted to receive a measuring signal of varying amplitude. The amplitude varies depending on the region of material being examined by the sensor physically within its detection range, and the amplitude of the measuring signal is increased by means of a controllable amplifier. The material to be investigated is furthermore moved relatively to the sensor such that the majority regions appear more frequently physically within the detection range of the sensor than do the minority regions. Conversely, of course, it follows that the minority regions appear physically within the detection range of the sensor less frequently than do the majority regions. The majority regions have a first thickness and a first material composition, and, correspondingly, the minority regions have a second thickness which differs from the first thickness and/or a second material composition which differs from the first material composition. A generic method is described, for example, in DE 10 2004 056 742.5.

Sensors for recognizing the thickness of web or sheet material should be capable of recognizing greatly deviating thicknesses and greatly deviating material compositions of the medium. In view of the fact that for example the temperature and relative humidity and other machine and environmental parameters can drift, such recognition is, in general, difficult to achieve. Thus, a "teach-in" (learning) phase is necessary, at least in the case of every change of medium. In addition, the sensitivity needs to be adapted to gradual effects caused by changes in temperature, barometric pressure, and humidity, and to variations in the material and/or other relatively slow processes.

In the prior art, two general solutions for this basic problem are proposed. The first approach uses a fixed switching threshold. This threshold can be immutable, or adjusted by means of a teach-in phase. To counter drifting of the kind described above, such a sensor signal requires comparatively complicated processing. This processing generally involves suitable further processing of the original test signal with the aid of characteristic curves and/or variable amplifications. DE 10 2004 056 742 describes this in some detail.

In this case, a variable switching threshold can be used, with either a fixed amplification during operation, or an amplification adjusted by using a teach-in phase. Adapting the switching threshold during operation is also a complicated undertaking.

SUMMARY

The present invention provides a less complicated method for metrologically differentiating regions of page-like, web-like or sheet-like material, and device therefor.

Embodiments of the method and device of the invention are described below, with reference to the figures.

The method mentioned above is characterized, according to the invention, in that during phases in which the sensor examines majority regions, the amplifier regulates the amplitude to a set point and generates a signal "majority region", and the sensor generates a signal "minority region" in situations in which there is a sufficient change in amplitude.

One concept of the present invention can be considered to be the adaptation of the method, more specifically than in the prior art, to metrological differentiation of materials, in which certain material regions occur more frequently and are thus referred to as majority regions, and other material regions occur comparatively less frequently and are thus referred to as minority regions.

Figure 3:
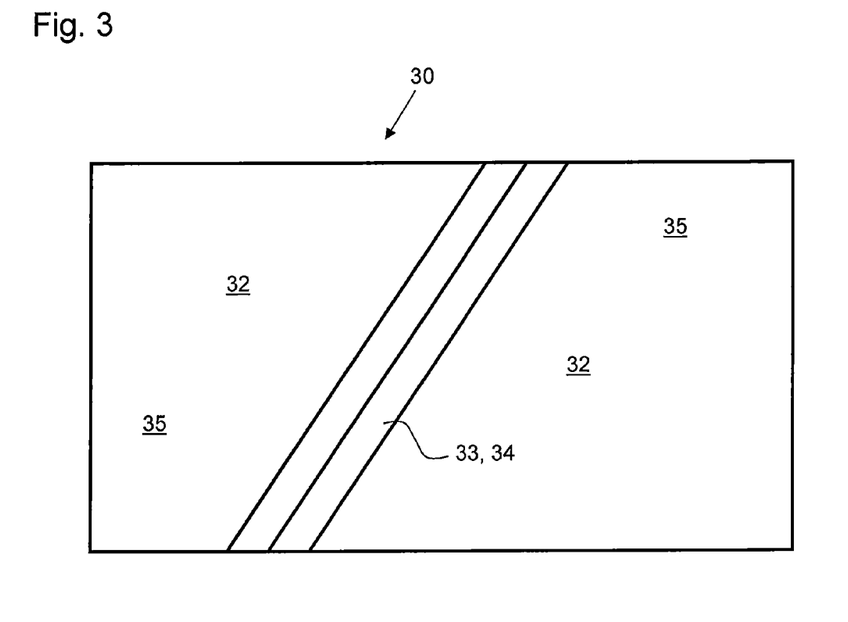
FIG. 3 is a second material, suitable for examination with the aid of the method of the invention.

FIG. 3 shows a first example thereof, this being a diagrammatic illustration of a material (30) having webs of paper or film as base material (32). In the example shown two sheets of the base material (32) are placed one beside the other and joined together with an adhesive tape (34). Since the base material (32) is found within the detection range of the sensor much more frequently than the adhesive tape (34), as can be seen directly from the ratio of the areas shown in FIG. 3, the base material is in this case identical to the majority regions (35) and the adhesive tape represents the minority regions (33). Such materials are frequently used in packaging technology, where a plurality of webs of paper or film material are joined together with the aid of an adhesive tape. This is necessary in order that a packaging machine need not be stopped when the paper rolls or film rolls are changed. Since, however, the adhesive tape is unwanted on the packaged end product, it is necessary to recognize the adhesive tape and to notify the machine control means with the ultimate goal of rejecting the region around the adhesive tape.

Figure 2:
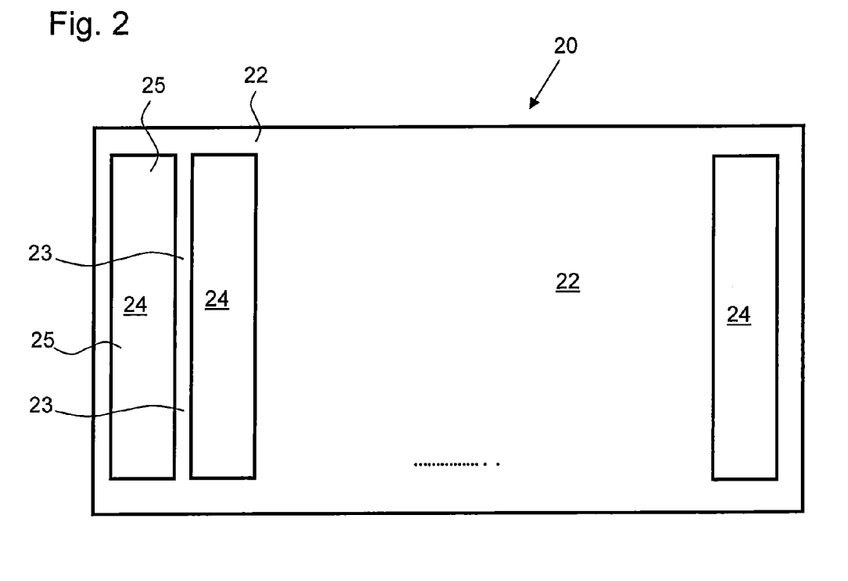
FIG. 2 is a first material, suitable for examination with the aid of the method of the invention.

Another example of material for which the method of the invention can be used to particular advantage is a sheet of paper or film to which adhesive labels have been applied. FIG. 2 is a diagrammatic illustration of such material. Many adhesive labels (24) are applied to a sheet of paper or film (20), which in this case represents the base material (22). The adhesive labels (24) have narrow spaces therebetween. The adhesive labels alternatively can be referred to as tags or stickers. Since the adhesive labels (24) are found much more frequently physically within the detection range of the sensor, also referred to simply as "detection range", the adhesive labels (24) in this case constitute the majority regions (25) and, correspondingly, the regions of base material (22) between the adhesive labels (24) represent the minority regions (23).

A further basic concept of the invention is that—based on the perception that the method should only be used for certain types of page-like, web-like, or sheet-like material, namely those, as clarified above, that have majority and minority regions—the amplitude of a measuring signal should be regulated to a set point followed by, simply speaking, waiting until the amplitude of the measuring signal changes significantly (e.g., until there is "sufficient" change in the amplitude), and to assume thenceforth that a minority region of the material being examined is in the detection range of the sensor.

Thorough investigation and testing have shown that this metrological principle is extremely reliable when used on material of the kind typically tested.

It can be seen that one advantage of the invention is that no teach-in phase of the sensor is required. This leads to a further advantage, namely that of a very simple design incorporating few components.

A further advantage of the invention is that gradual amplitude changes resulting from changing ambient conditions, such as changes in temperature, barometric pressure, and humidity, and other parameters subject to gradual variation, are continually compensated for by means of the regulation principle proposed herein.

In general, the regulation to the set point can always remain enabled, particularly when the minority regions appear only briefly in the detection range of the sensor.

The method of the invention can be used in significantly more contexts if, in situations in which the sensor generates the signal "minority region", the regulation of the amplitude to the set point is deactivated. This ensures that the method also functions reliably with a slow feed rate of the base material, for example, a paper or film, and when, accordingly, an adhesive tape or a gap between two adhesive labels is in the detection range of the sensor for a comparatively long period of time. Without deactivation of such regulation, the amplitude would again be regulated to the set point. For example, the adhesive tape would then be recognized as base material, which is incorrect. In such cases, it is therefore preferable for the regulation to be deactivated when the sensor generates the signal "minority region". This is achieved, according to the invention, in that the regulating means monitors the amplitude of the measuring signal and carries out appropriate regulations.

In this context it is further preferable, in situations in which the regulating means has been deactivated and in which there is a sufficient change in amplitude in the opposite direction to that of the most recent change that led to deactivation of the regulation, for the regulation to be reactivated and for the sensor to generate the "majority region" signal. This ensures that the method proceeds reliably.

In general, the definition of a "sufficient change" can be basically stipulated as desired. The amplitude is adjusted to the set point in those phases in which the sensor is examining majority regions. The method is particularly simple to carry out when it is based on the assumption that a sufficient change in amplitude has occurred when the amplitude deviates from the aforementioned set point by more than a fixed amount.

Correspondingly, during a "sufficient change" of the amplitude in phases in which the sensor generates the "minority region" signal, such a "sufficient change in amplitude" can be considered to have occurred when the amplitude deviates by less than a definable amount from the set point to which the amplitude is adjusted in those phases in which the sensor examines majority regions.

In other words, a change in amplitude qualifies as being "sufficient" when, starting from those phases in which the sensor is signaling a "minority region" the change moves close to the set point within a suitably chosen interval, or, in those cases in which the sensor is signaling a "majority region", when it moves out of a suitably chosen interval surrounding the set point.

In order that the method can be started as soon as material is fed for examination, it is advantageous for the sensor to receive information via a sensor configuration means or via a control input before commencing measurement, so as to ascertain whether the amplitude of the measuring signal rises or falls when moving from a majority region to a minority region.

The method of the invention can be employed to particular advantage when the material to be examined is a web of paper or film having adhesive tapes or spot, or when the material is a web of paper or film with adhesive labels applied thereto.

These two materials are used frequently in packaging and automation technology.

In phases in which the sensor is examining majority regions, the regulation of the amplitude to the set point can be done for example with the aid of a PID (proportional-integral-derivative) controller. An embodiment of the method is characterized in that the regulation of the amplitude to the set point is achieved by calculating a mean value for a number of amplitude measurements already carried out, and, when this mean value is above the set point, by reducing the degree of the amplification by one unit, and continuing the regulation with this amplification, and that when this mean value is below the set point, the degree of amplification is increased by one unit and regulation is continued with this strength of amplification.

Compared with a classical proportional-integral-differential (PID) controller, this regulation has an advantage that less computation is necessary and that the regulation is, in general, independent of the magnitude of the fluctuations in amplitude.

A special case for such regulation is a situation in which the examined material, for example a web of paper or film, is changed. Not infrequently, the paper fed to a single machine may be changed, say, several times a day. In this context, an embodiment of the method is one which, in situations where the amplitude takes on its maximal value for a configurable period of time, the sensor assumes that no material is physically present within its spatial detection range. The amplifier is then adjusted to its minimum amplification. The regulating means remains active and continues to attempt to move the amplitude to the set point. This fails, however, since even at the minimum possible amplification the amplitude will still be significantly above the set point. This mode is exited only when the amplitude falls, more particularly, when the amplitude of the measuring signal deviates from the maximal amplitude by a configurable amount. This may be the case, for example, when material is again fed to the detection range of the sensor.

With this variant of the method, it is possible to recognize the absence of material in the spatial detection range of the sensor over a certain period of time. When this period of time has elapsed, the regulating means activates a paper change mode, or less specifically, a material change mode.

In general, all sensors capable of differentiating majority regions from minority regions on the materials discussed herein can be used. Barrier sensors or sensors adapted to measure reflected light may basically be used for this purpose. However, ultrasonic or capacitive sensors are preferred, and here again barrier sensors or reflective sensors can be used.

Using the materials described above, that is, "paper with adhesive tapes" on the one hand and "paper with adhesive labels" on the other, the base material (i.e. the paper) is the "majority region" in the first case but the "minority region" in the second case. To avoid ambiguities that may possibly arise for a user because of this, a variant of the method is advantageous in which the signals "adhesive spot," "adhesive label" and/or "base material" are generated according to the following criteria:

When examining material producing a decrease in amplitude on moving from a majority region to a minority region (e.g. when recognizing adhesive spots), the signal "base material" will be generated when the sensor additionally generates the signal "majority region", and the signal "adhesive spot" will be generated when the sensor additionally generates the signal "minority region". On the other hand, when examining material producing an increase in the amplitude on moving from a majority region to a minority region (e.g. when recognizing amplitude), the signal "base material" will be generated when the sensor additionally generates the signal "minority region", and, on the same material, the sensor will generate the signal "adhesive label", when it additionally generates the signal "majority region".

For the purposes of the present invention, the terms "generating" and, synonymously, "signaling", should be taken to mean in general terms the provision of a corresponding signal, which may be outputted, for example as "majority region," "minority region," "base material," "adhesive spot," "adhesive label," and "material change," at, for example, separate outlets of the sensors. This information can then be utilized by a higher-level unit to make it accessible, more particularly visually, to a user.

BRIEF DESCRIPTION OF THE DRAWINGS

Further advantages, features, and properties of the present invention will be described below with reference to the enclosed drawings.

Identical or identically-functioning components and items are usually designated by the same reference numerals.

DETAILED DESCRIPTION

Figure 1:
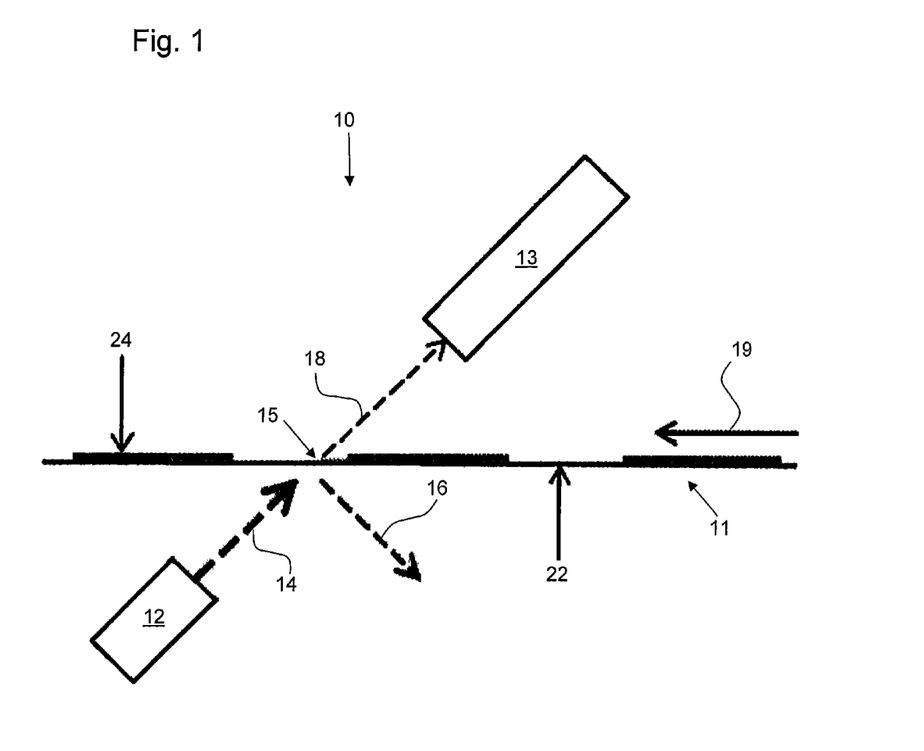
FIG. 1 is a diagrammatic view of a measurement assembly suitable for carrying out the method of the invention.

The basic measurement situation will now be explained with reference to FIG. 1. FIG. 1 illustrates a barrier sensor 10 having a transmitter 12 and a receiver 13. FIG. 1 is a diagrammatic illustration. In reality, the sensor 10 has further components, for example, a micro-controller or a similar component, which controls measurement recordings and the evaluation thereof. Here, the configurable amplifier component of the sensor 10, provided according to the invention, is also not shown. The example shown in FIG. 1 is of an ultrasonic sensor, i.e. the transmitter 12 emits ultrasonic waves 14 in the direction of a material 11 to be examined, which material is, in the example shown, a web 22 of paper or film. The ultrasonic emission 14 transmitted by the transmitter 12 encounters the material 11 within the spatial detection range 15 of the sensor and is reflected and transmitted therefrom. The portion of the ultrasonic emission reflected is represented by an arrow 16 in FIG. 1. An arrow 18 passing to the receiver 13 represents the transmitted and attenuated portion of the ultrasonic emission. In the case shown in FIG. 1, part of the web 22 of paper or film, in this case also named as base material 22, is present in the detection range 15 of the sensor. Adhesive labels 24 have been applied to the base material 22. The purpose of the measurement is to ascertain whether a part of the base material 22 or an adhesive label 24 is within the spatial detection range 15 of the sensor 10. To this end, the sensor 10 and the material 11 are continually moved relatively to each other. This is demonstrated in FIG. 1 by the arrow 19.

In those places where, as shown in FIG. 1, an adhesive label 24 or an adhesive spot (not shown in FIG. 1) is found on the material, the ultrasonic waves are attenuated still further, so that the amplitude of the measuring signal of the receiver 13 is decreased. The basic concept of the invention is to identify the adhesive label 24 or an adhesive tape by way of these changes in amplitude.

FIG. 1 accordingly shows a sensor that makes it possible to detect the presence of adhesive labels 24 on a base material 22. In doing so, the sensor 10 reacts to the gaps between two adhesive labels 24. Since these gaps can be very small, a quick response time of significantly less than one millisecond may be required.

Figure 4:
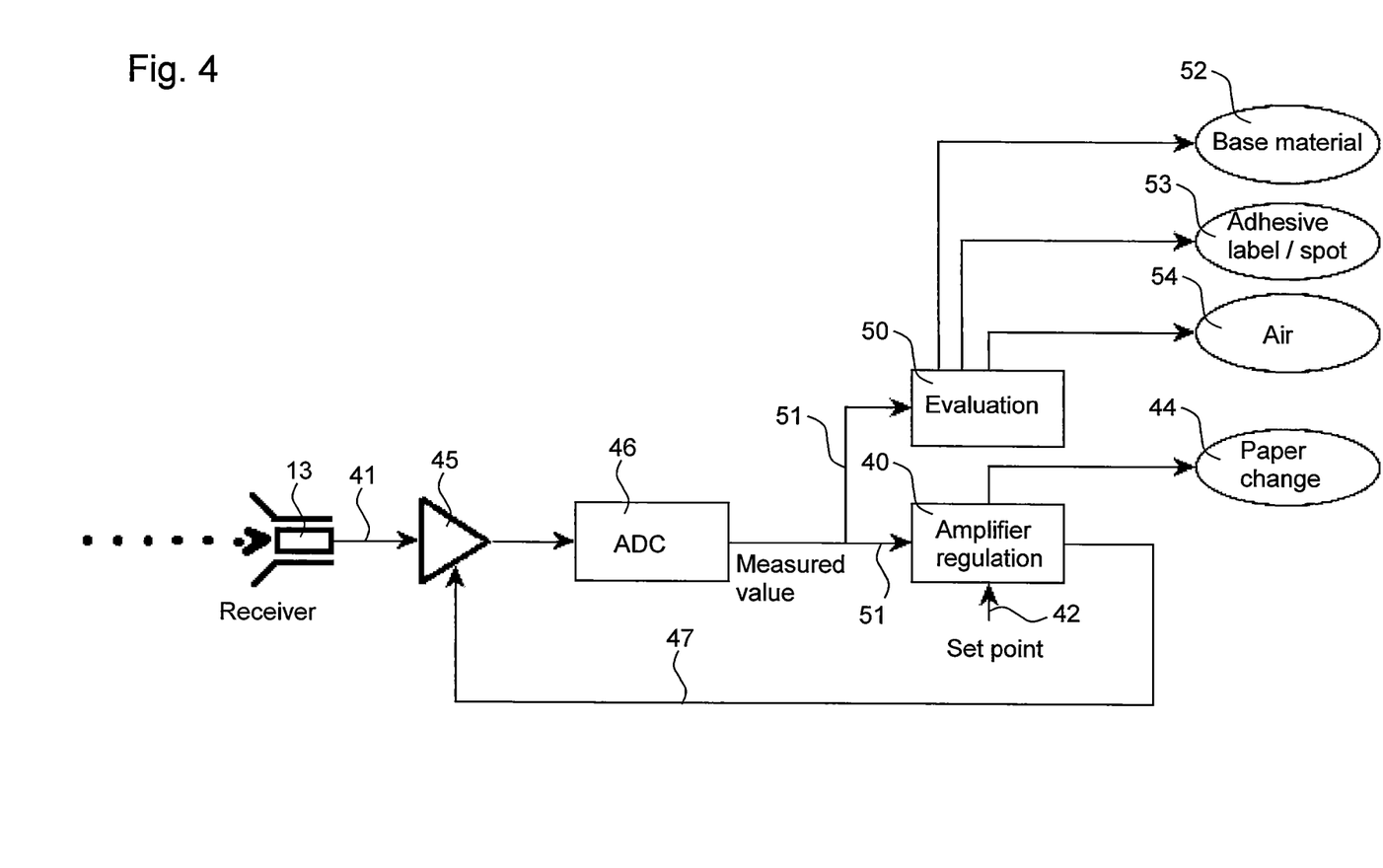
FIG. 4 is a diagrammatic illustration of a regulation process that can be used in the method of the invention, and also a variant of an evaluation process that can be used in the method of the invention.

FIG. 4 is a diagrammatic illustration of the basic course of events for regulating the amplifier. This regulating means is illustrated diagrammatically as a box 40 in FIG. 4. Control of the amplifier 45 by the regulating means 40 is demonstrated by means of an arrow 47. A real measured amplitude (arrow 41) of the measuring signal from the sensor receiver 13 used is supplied as input data to the amplifier 45. A set point 42 is, in addition, supplied to the regulating means 40, to which set point the amplitude should be regulated if a majority region 25, 35 is present in the detection range 15 of the sensor 10. The amplification achieved by the amplifier 45 depends on the setting of a digital potentiometer (not shown). The regulating means 40 sets the digital potentiometer according to the adjusted parameters of the regulating means.

As already described in detail, the amplifier can be active, typically when majority regions are being examined, or it can be deactivated, which is the case, for example, when there is nothing within the spatial detection range of the sensor or when a minority region is being examined.

Since the state "paper change" is characterized by minimal amplification, the regulating means 40 can be queried directly for this state, or the regulating means 40 can generate it. The generation of the state "paper change" is designated by the reference numeral 44 in FIG. 4.

The amplification can be adjusted by the digital potentiometer using software. As illustrated diagrammatically in FIG. 4, the regulating means 40 thus receives a currently measured value and a set point 42 following each analog-digital conversion in the analog-digital converter (ADC) 46, to which set point 42 the amplitude is to be regulated. The aim is to regulate the amplification in such a way that the mean amplitude is equal to the given set point over a plurality of measurements. By way of example, simple addition to, or subtraction from, the amplification can be used as the regulation algorithm. This means that if the mean value is above the set point, the amplification is decreased by one unit or by one digit. On the other hand, if the mean value is below the set point, the amplification is increased by one unit or by one digit.

This regulation should not be carried out too quickly, since any sudden fall in amplitude, for example when detecting an adhesive spot, should not be regulated off too quickly. Conversely, the regulation should also not be carried out too slowly, since, as clarified above, the sensor's maximum response time should not exceed one second.

In addition, FIG. 4 shows, in abstracted form, features of the evaluation 50, represented in FIG. 4 diagrammatically by a box. The evaluation process 50 involves steps of the method of the invention following receipt of the measurement data by the sensor 10. These measurement data, basically the amplitude of the measuring signal, are supplied to an evaluation process 50, illustrated in FIG. 4 by the arrow 51. The evaluation process 50 evaluates these data in accordance with previously applied settings and generates signals according to the successive steps of the method of the invention. In the example shown in FIG. 4 these are the signals "Base material" 52, "Adhesive label/spot" 53, and "Air" 54, which is equivalent to "paper change" or "material change".

Figure 5:
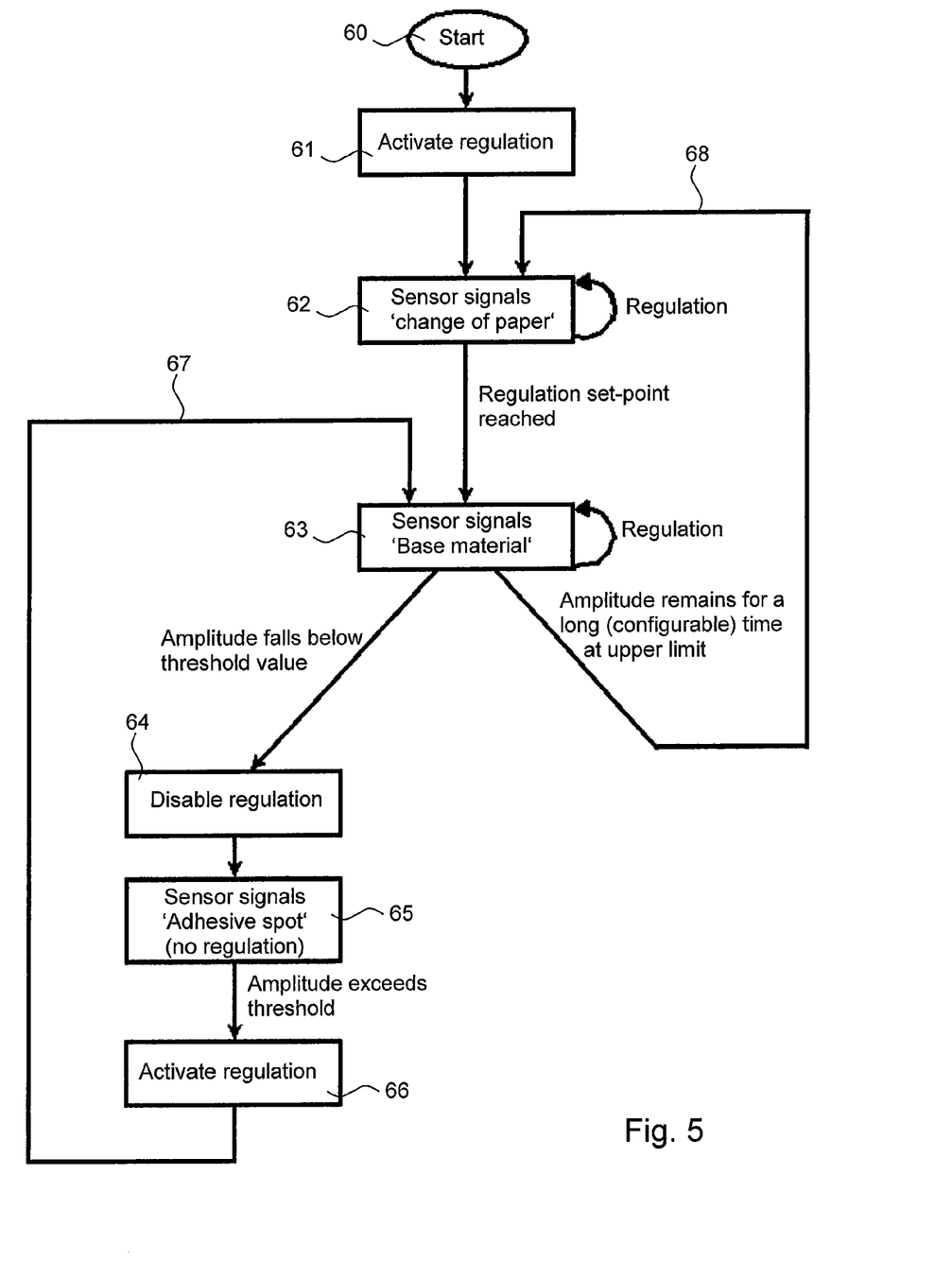
FIG. 5 is a diagrammatic illustration of a flowchart of the method of the invention for a material with which the amplitude of the measured value decreases on moving from a majority region to a minority region.
Figure 6:
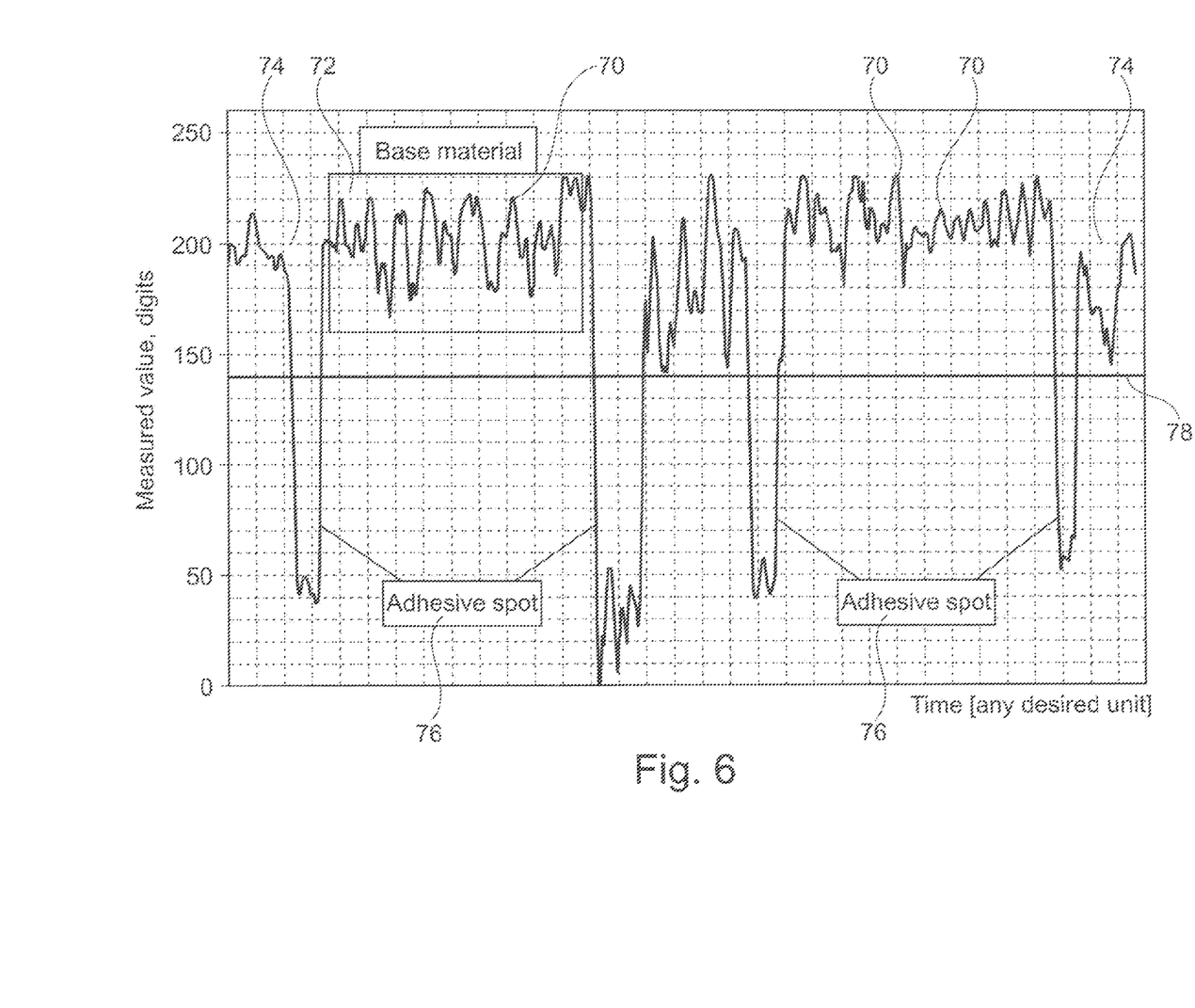
FIG. 6 is a graph illustrating the amplitude of the measuring signal plotted as a function of time in the context of the measurement situation described with reference to FIG. 5.

The course of the method of the invention will be explained in more detail below with reference to FIGS. 5 and 6. FIGS. 5 and 6 illustrate a variant of the method for recognizing adhesive spots. In FIG. 6 a graph of the amplitude 70 of the measuring signal in any desired unit (digits) is plotted as a function of time (again in any desired unit). FIG. 6 also shows a set point 74 and a threshold 78.

In the prior art, fixed switching thresholds are defined for the sensors. When the measured amplitude under-runs this threshold, the sensor switches to one output. Since papers differ in the extent to which they attenuate the signal, these sensors need a teach-in phase during which the measured amplitude for the respective base material, for example paper, is learned, and the switching threshold is then typically set to 30% above or below this signal, according to whether adhesive labels or adhesive spots are to be recognized.

Since the amplification provided by the method of the invention is controlled by a regulating means, the amplitude of the measuring signal remains at the same value, irrespective of the examined material 11. A significant advantage of the present invention is thus achieved in that a teach-in phase is no longer necessary. For example, as seen in FIG. 6, the amplitude 70 of the measuring signal can be regulated to a set point 74 with a value of, for example, 200 digits.

In phases in which the majority regions 35 of the material 30 (see FIG. 3) are being examined, the mean value of the amplitude 70 is adjusted to 200 digits. This is shown by way of example in FIG. 6 in box 72, where the amplitude 70 fluctuates about the value of 200 digits. Additionally, in FIG. 6 four regions can be recognized where the amplitude 70 falls below the threshold 78, which in this case indicates a sufficient change in amplitude when compared with the set point 74. These four regions are shown in the two boxes 76.

The problems arising with a fixed switching threshold become clear at those points where the profile of the amplitude 70 comes very close to the threshold 78 without under-run. The probable reason for these very low values of the amplitude 70 is a lack of homogeneity of the material 30. Thus, at these points, there is a significant risk of the sensor being switched incorrectly.

The course of embodiments of the method of the invention for the example of recognizing adhesive spots is described below with reference to FIG. 5:

Once the sensor is started at 60, the regulating means is activated, and the sensor signals "change of paper" or "change of material" in step 62 of the method. At the same time, the sensor attempts to regulate to a set point, which has already been communicated to the sensor or which is known. As long as no material is present in the detection range of the sensor, it will not be possible to regulate the amplitude to this point, since even with the smallest possible amplification the amplitude 70 of the signal will be above the set point 74. As soon as a material 30 to be examined (see FIG. 3) has been placed in the detection range 15 of the sensor 10, regulation to the set point becomes possible and the set point 74 can be reached. The sensor then generates the signal "base material" in step 63 of the method. The system remains in this state until the amplitude 70 of the measuring signal falls below the threshold 78 and consequently, a sufficient change in amplitude has occurred. This brings the system to step 64 of the method, at which point the regulation is deactivated. At this stage, the amplification can be maintained at the value last determined or set. The sensor then generates the signal "adhesive spot" (step 65 in FIG. 5).

Here it is important that the regulation take place in the majority regions 25, 35 (see FIGS. 2 and 3), i.e. those material regions that are in the detection range of the sensor more frequently than other material regions. As can be seen from FIG. 3, when recognizing adhesive spots, the majority regions are the regions of base material 32. On the other hand, when recognizing labels, the labels 24 themselves constitute the majority regions 25 (see FIG. 2).

When examining material 20 where labels 24 have been applied to a base material 22, as in FIG. 2, and starting from step 63, where the sensor would generate a signal "Adhesive label", the amplitude would increase.

In the example shown in FIG. 5, step 64 is followed by step 65, in which the sensor generates the signal "Adhesive spot" and deactivates the regulation.

When recognizing labels, the sensor would at this point generate the signal "Base material" instead of the signal "Adhesive spot".

Returning to FIG. 5: as soon as the amplitude 70 of the measuring signal exceeds the threshold value 78 again, the regulation is re-activated in step 66, and the method loops back to step 63, as indicated by the arrow 67, so that the sensor will generate the signal "Base material". Accordingly, steps 64, 65, and 66 are run through every time a minority region is present in the detection range of the sensor. In the example shown in FIG. 5, this is an adhesive spot and if the method is used to recognize labels, here will be a small region of base material between the labels.

A special case, that nevertheless may occur frequently, results in the situation when there is a change of paper or other material. For example, some machines require the paper to be changed several times a day. The method of the invention makes it possible for this situation to be recognized, since in this case there is no material in the detection range of the sensor for a certain period of time. Thus, when the amplitude remains at or near the upper threshold value for a freely selectable and adjustable period of time, the sensor will pass back to step 62 of the method, at which point it will signal "Change of material" or "Change of paper", as indicated in FIG. 5 by the arrow 68, and it will also attempt to regulate the amplitude to the set point 74. The signal outputs "Adhesive spot" and "Base material" are deactivated and remain deactivated as long as the method remains in step 62. However, either "Change of paper" or "Change of material" will be signaled.

The amplifier remains at the lowest degree of amplification, so that the amplitude 70, in the absence of material 20, 30 (see FIGS. 2 and 3) in the detection range of the sensor, remains at full-scale deflection. The restricted degree of amplification ensures that the amplitude 70 falls very sharply even with material that causes a very weak muffling effect. Thus, the regulating means can reliably recognize when material such as paper, for example, reappears in the spatial detection range of the sensor 10. The amplitude 70 is then again regulated to the set point 74. Once the set point 74 has been reached, the method proceeds to method step 63 followed by the method steps described above.

It may be preferable to use a sensor which makes it possible to carry out all configuration steps for the regulation process from a computer using, for example, an infra-red interface, or theoretically, any other type of interface.

The present invention provides a novel method for recognizing, on the one hand, labels, and on the other, adhesive spots and adhesive strips. The invention can be applied to material sensors, which in operation are required to differentiate between two distinct medium thicknesses, which differentiation should be possible on a large range of medium thicknesses and a great variety of medium materials. Changing from one material region to the other should take place as quickly as possible. For this reason, the solution provided by the invention is most suitable for recognizing labels and adhesive spots. To summarize, a method is provided which makes it possible to differentiate between two amplitude values using a switching output, without any need for a teach-in phase for one or other of the two amplitudes.

This quick change between the material regions provides a trigger signal for the sensor, which effects a change in the automatic calibration: the sensor starts from a default scenario and regulates with variable amplification the amplitude of the measuring signal on the detection scale of a comparator having a switching threshold, more particularly a fixed switching threshold. This automatic calibration functions continuously.

The default scenario involves regulation taking place for those material regions which are present most frequently in the detection range of the sensor, that is to say, the majority regions. In the case of the recognition of labels, the labels themselves form the majority regions. For recognition of adhesive spots, the majority regions constitute the paper or in any case the base material, as is immediately clear from a consideration of the area ratios.

When a change has to take place, as described above, the amplitude is initially no longer regulated, and the sensor can then differentiate between adhesive spot and base material or between labels and base material. On the basis thereof, automatic calibration will then proceed continuously until the next change of material occurs.

Furthermore, a particular advantage of the method is achieved in that the continuous automatic calibration means that interference occurring between changes is compensated for.

The invention claimed is:

1. A method for metrologically differentiating material regions, namely majority regions and minority regions of a page-like, web-like, or sheet-like material, comprising:
producing, by a sensor, a measuring signal of variable amplitude, the amplitude of the measuring signal produced by the sensor varies depending on the material region located in a spatial detection range of the sensor and examined by means of the sensor,
increasing the amplitude of the measuring signal produced by the sensor by means of an adjustable amplifier,
moving the material to be examined relatively to the sensor such that the majority regions are located in the spatial detection range of the sensor more frequently than the minority regions,
the majority regions have a first thickness and a first material composition,
the minority regions have a second thickness differing from the first thickness and/or a second material composition differing from the first material composition,
wherein
in phases, in which majority regions undergo examination by means of the sensor, regulation of the amplitude to a set point is carried out by means of the amplifier and a majority region signal is generated by the sensor, and
when the amplitude undergoes a sufficient change, a minority region signal is generated by the sensor,
wherein
an adhesive spot signal, an adhesive label signal, and a base material signal are generated by the sensor according to the following conditions:
a) when a material is being examined, in the case of which the amplitude drops when passing from a majority region to a minority region,
a1) the base material signal is generated, if the sensor in addition generates the majority region signal; and
a2) the adhesive spot signal is generated, if the sensor in addition generates the minority region signal;
b) when a material is being examined, in the case of which the amplitude rises on passing from a majority region to a minority region,
b1) the base material signal is generated if the sensor in addition generates the minority region signal; and
b2) the adhesive label signal is generated if the sensor in addition generates the majority region signal.

2. The method as defined in claim 1,
wherein
a sufficient change in the amplitude is present when the amplitude deviates from the set point by more than a configurable amount, to which set point the amplitude is regulated in the phases in which majority regions undergo examination by means of the sensor.

3. The method as defined in claim 1,
wherein
when the sensor generates the minority region signal, the regulation of the amplitude to the set point is deactivated.

4. The method as defined in claim 3,
wherein
when regulation is deactivated and the amplitude has sufficiently changed in an opposite direction to that occurring during the last change leading to deactivation of the regulation, the regulation is reactivated and the sensor generates the majority region signal.

5. The method as defined in claim 3,
wherein
when regulation is deactivated and the amplitude has sufficiently changed in an opposite direction to that occurring during the last change leading to deactivation of the regulation, the regulation is reactivated and the sensor generates the majority region signal, and
a sufficient change in the amplitude is present when the amplitude deviates from the set point by less than a configurable amount, to which set point the amplitude is regulated in those phases in which majority regions undergo examination by means of the sensor.

6. The method as defined in claim 1,
wherein
the sensor receives information via a sensor configuring means or via a control input prior to commencement of the measuring procedure as to whether the amplitude of the measuring signal has dropped or risen on passing from a majority region to a minority region.

7. The method as defined in claim 1, wherein
the material to be examined is a sheet of paper or film comprising an applied adhesive strip or adhesive spot or
the material to be examined is a sheet of paper or film comprising applied labels.

8. The method as defined in claim 1, wherein
the regulation of the amplitude to the set point is carried out in that an average of a number of previous measurements of the amplitude is ascertained, and
when the average is above the set point, the degree of amplification is reduced by one unit and the regulation is continued at this amplification, and
when the average is below the set point, the degree of amplification is raised by one unit and the regulation is continued at this amplification.

9. The method as defined in claim 1, wherein
when the amplitude assumes a maximum possible value over a configurable period of time, the sensor assumes that there is no material in the spatial detection range of the sensor.

10. The method as defined in claim 1, wherein
the sensor used is a capacitive sensor or an ultrasonic sensor.

11. The method as defined in claim 1, wherein
the sensor used is a barrier sensor or a reflective sensor.

12. A device for carrying out the method as defined in claim 1.

* * * * *